US009611476B2

(12) United States Patent
Leschinsky

(10) Patent No.: US 9,611,476 B2
(45) Date of Patent: Apr. 4, 2017

(54) CANCER TREATMENT METHODS USING REMOTE CONDITIONING

(71) Applicant: LifeCuff Technologies Inc., Waldwick, NJ (US)

(72) Inventor: Boris Leschinsky, Mahwah, NJ (US)

(73) Assignee: LifeCuff Technologies Inc., Waldwick, NJ (US)

( * ) Notice: Subject to any disclaimer, the term of this patent is extended or adjusted under 35 U.S.C. 154(b) by 0 days.

(21) Appl. No.: 14/847,191

(22) Filed: Sep. 8, 2015

(65) Prior Publication Data
US 2016/0068841 A1    Mar. 10, 2016

Related U.S. Application Data

(60) Provisional application No. 62/048,634, filed on Sep. 10, 2014.

(51) Int. Cl.
| A61K 48/00 | (2006.01) |
| C07H 21/04 | (2006.01) |
| C12N 15/113 | (2010.01) |
| A61K 31/7088 | (2006.01) |
| A61K 45/06 | (2006.01) |
| A61K 31/00 | (2006.01) |
| A61N 5/06 | (2006.01) |
| A61N 5/10 | (2006.01) |

(52) U.S. Cl.
CPC ............ *C12N 15/113* (2013.01); *A61K 31/00* (2013.01); *A61K 31/7088* (2013.01); *A61K 45/06* (2013.01); *A61N 5/0613* (2013.01); *A61N 5/10* (2013.01); *C12N 2310/141* (2013.01); *C12N 2320/30* (2013.01); *C12N 2320/31* (2013.01)

(58) Field of Classification Search
CPC . A61K 48/00; C12N 2310/11; A61B 17/1355
See application file for complete search history.

(56) References Cited

U.S. PATENT DOCUMENTS

2012/0134966 A1*  5/2012  Blelloch ............... A61K 35/545
                                                           424/93.7
2012/0165259 A1*  6/2012  Ueda ................... A61K 38/2292
                                                            514/12.9

FOREIGN PATENT DOCUMENTS

WO   WO 2006/014158 A1 *  2/2006  ........... C12N 15/113
WO       2012140234        10/2012
WO       2014140911         9/2014

OTHER PUBLICATIONS

Kovalchuk O. et al. Involvement of microRNA-451 is resistance of the MCF-7 breast cancer cells to chemotherapeutic drug doxorubicin. Mol Cancer Ther 2008;7(7).

Iwaya T et al. Downregulation of mir-144 is associated with colorectal cancer progression via activation of mTOR signaling pathway. Carcinogenesis 33(12):2391-2397, 2012.
Li Hy et al. MicroRNA-451 inhibits growth of human colorectal carcinoma cells via downregulation of Pi3k/Akt pathway. Asian Pacific J Cancer Prev 14(6):3631-3634, 2013.
Akiyoshi S. et al. Clinical significance of miR-144-ZFX axis in dissemination tumour cells in bone marrow in gastric cancer cases. British J Cancer 107(8):1345-1353, 2012.
Hui A.B.Y. et al. Comprehensive microRNA profiling for head and neck squamous cell carcinomas. Clin Cancer Res 16(4):1129-39, 2010.
Bian H.B. et al. Upregulation of microRNA-451 increases cisplatin sensitivity on non-small cell lung cancer cell line (A549). J Exp Clin Cancer Res 30(20):1-11, 2011.
Zha W. et al. Roles of Mir-144-ZFX pathway and growth regulation of non-small-cell lung cancer. PlosOne 8(9): e74175, 2013.
Li J. et al. MicroRNA-144 is a circulating effector of remote ischemic preconditioning. Basic Res Cardiol 109:423, 2014.
Liu D. et al. MicroRNA-451 suppresses tumor cell growth by down-regulating IL6R gene expression. Cancer Epidemiology 38:85-92, 2014.
Othman N, Nagoor NH. The role of microRNAs in the regulation of apoptosis in lung cancer and its application in cancer treatment. BioMed Research International, vol. 2014, Article ID 318030, 2014.
Liu n. et al. MiR-451 inhibits cell growth and invasion by targeting MIF and is associated with survival in nasopharyngeal carcinoma Molecular Cancer 12:123, 2013.
Pan X. et al. The potential role of miR-451 in cancer diagnosis, prognosis and therapy. Mol Cancer Ther 12(7):1-10, 2013.
Wang X. et al. Loss of the miR-144/451 cluster impairs ischaemic preconditioning-mediated cardioprotection by targeting Rac-1. Cardiovascular Research 94:379-390, 2012.
Jiang Q, Yu T, Huang K, Lu J, Zhang H, Hu S. Remote ischemic postconditioning ameliorates the mesenchymal stem cells engraftment in reperfused myocardium. PLOS ONE 11(1):e0146074, 2016.
Kamota T et al. Ichemic preconditioning enhances the mobilization and recruitment of bone marrow stem cells to protect against ischemia/reperfusion injury in the late phase. JACC 53;19:1814-1822, 2009.
WebMD printout Dec. 1, 2016. Bone Marrow Transplants and Stem Cell Transplants for Cancer Treatment. (http://www.webmd.com/cancer/lymphoma/bonemar-rowtransplantsstemcelltransplantscancertreatment? print=true), 2016.

* cited by examiner

Primary Examiner — Amy Bowman
(74) Attorney, Agent, or Firm — Boris Leschinsky

(57) ABSTRACT

Cancer treatment methods comprising a step of applying remote conditioning to the cancer subject, for example remote ischemic conditioning via several episodes of short-term limb occlusion. Upregulation and release of remote conditioning substances such as microRNA 144/451 cluster endogenously caused by remote conditioning may be beneficial in reducing the growth and proliferation of malignant cells. Remote conditioning may also be beneficial when combined with chemotherapy or radiation therapy as it may improve survival of healthy surrounding tissues and minimize side effects of these known cancer treatments. Remote conditioning may be non-invasively applied by a medical professional or self-applied by the cancer subject at home using an automatic device. The novel cancer treatment methods may be used for lung cancers, liver cancers, colorectal cancers, digestive cancers and other cancers.

4 Claims, No Drawings

CANCER TREATMENT METHODS USING REMOTE CONDITIONING

CROSS-REFERENCE DATA

This application claims a priority date benefit of the U.S. Provisional Patent Application No. 62048634 filed 10 Sep. 2014 with the same title and incorporated herein in its entirety by reference.

BACKGROUND OF THE INVENTION

The present invention relates generally to cancer treatment methods. More particularly, the invention describes exposing a cancer subject to a remote conditioning procedure. As a result of such procedure, certain biologically active substances may be upregulated or released that may beneficially affect the cancer subject such as for example slow the proliferation of malignant cells throughout the body of the cancer subject.

Cancer is a group of diseases involving abnormal cell growth and proliferation. In 2012 about 14.1 million new cases of cancer occurred globally. It caused about 8.2 million or 14.6% of all human deaths. The most common types of cancer in males are lung cancer, prostate cancer, colorectal cancer, and stomach cancer, and in females, the most common types are breast cancer, colorectal cancer, lung cancer, and cervical cancer. Skin cancer is not included in these statistics and if it were it would account for at least 40% of cases. The financial costs of cancer have been estimated at $1.16 trillion US dollars per year as of 2010. Despite tremendous progress in the treatment methods, cancer subjects continue to experience pain and suffering as well as early death as a result of this disease necessitating further research into treatment modalities.

Two most widely used treatment methods for various cancers include radiation therapy and chemotherapy. However, these treatments have significant side effects as they affect both malignant as well as healthy cells. Indiscriminate cell death causes both a health benefit (tumor suppression) as well as harm caused by loss of healthy tissues. New treatment methods are therefore needed that do not cause harm to the cancer subject while continuing to provide health benefits.

Cancer in general is known to have five major development steps: initiation, promotion, malignant conversion, progression, and metastasis. Many factors influence the development and proliferation rate of cancers: some inhibit tumor development (tumor suppressors), and some promote cancer development (cancer inducers). The formation of cancer is the combined interaction of both tumor suppressors and cancer inducers. Scientists have been trying to elucidate the molecular mechanisms that cause cancer development and cancer prevention for a long time. Although several genes, including oncogenes and tumor suppressor genes, have been identified in human and/or other model animal genomes, the exact mechanism of cancer formation is yet to be identified. A recently identified class of non-protein-coding small RNAs, microRNAs (also referred to as miRNAs or miR), may provide new insight in cancer research. A recent study demonstrated that more than 50% of miRNA genes are located in cancer-associated genomic regions or in fragile sites, suggesting that microRNAs may play an important role in the pathogenesis of human cancers.

When cells exhibit abnormal growth and loss of apoptosis function, it usually results in cancer formation. Several recent studies indicate that microRNAs regulate cell growth and apoptosis. For example, microRNA-15 and microRNA-16 induce apoptosis by targeting antiapoptotic gene B cell lymphoma 2 (BCL2) mRNA, which is a key player in many types of human cancers, including leukemias, lymphomas, and carcinomas. Also demonstrated was that aberrant expression of microRNA-278 in developing eyes causes massive overgrowth in Drosophila, partially due to inhibition of apoptosis by miR-278. This suggests that microRNAs are involved in cancer formation through regulation of cell growth and apoptosis.

Lung cancer is one of the most common cancers of adults. It is also the leading cause of cancer-related deaths in many economically developed countries. Emerging evidence suggests that at least microRNA let-7 and perhaps others may control lung cancer development, or at least play a critical role in its pathogenesis. Another example of microRNA involvement comes from breast cancer research. Breast cancer is one of the most important cancers in adult females. Evaluation of hundreds of microRNA expression profiles led to a discovery that the microRNA expression patterns were significantly different between normal and neoplastic breast tissues; microRNA-125b, microRNA-145, microRNA-21, and microRNA-155 were shown to be significantly reduced in breast cancer tissues. Also observed was the fact that the expression of microRNAs was correlated with specific breast cancer bio-pathologic features, such as tumor stage, proliferation index, estrogen and progesterone receptor expression, and vascular invasion.

Evidence continues to emerge that aberrant expression of various microRNAs (whether increased or decreased levels as compared with normal tissues) plays a major role in tumor growth and spreading.

Because microRNAs function as oncogenes or tumor suppressors, it might be possible to inject microRNAs to regulate cancer formation, similar to the use of antisense mRNAs and RNAi, which are widely used as tools for studying gene functions and in some case of gene therapy. Artificial microRNAs could be synthesized to down-regulate oncogenes and prevent the formation of cancer. In fact, some short-term animal studies have confirmed that hypothesis. However, there is a long way to go before artificial microRNAs could be used as cancer therapeutic tools and microRNA therapy for clinical purposes. To achieve this goal, several obstacles need to be overcome. First, specific microRNAs in a specific type of cancer should be identified; only when the specific microRNAs are identified and their action mechanisms were elucidated in a specific cancer, physicians can manipulate these microRNAs for therapeutic purposes. How to deliver these microRNAs into targeted tissues and keep their continuous activity is another obstacle. It may also be quite difficult to manufacture such compounds in a form of an ingestible pill as microRNAs may not survive the harsh acidic environment of the digestive system. Finally, safety considerations need to be addressed as various microRNAs may have an impact on various genes elsewhere in the body of the cancer subject.

Accordingly, there is a need to overcome the limitations of the prior art and to provide novel cancer treatment methods designed to minimize healthy tissue damage or other negative health consequences of traditional cancer treatments, while providing meaningful health benefits to the cancer subject.

There is also a need to provide safe, non-invasive novel cancer treatment methods that can be applied to cancer subjects by medical professionals or even self-applied.

SUMMARY OF THE INVENTION

Accordingly, it is an object of the present invention to overcome these and other drawbacks of the prior art by providing novel cancer treatment methods by subjecting the cancer subject to a remote conditioning therapy.

It is another object of the present invention to provide novel cancer treatment methods that are non-invasive so as to improve safety profile for the cancer subject.

It is a further object of the present invention to provide novel cancer treatments with minimum or no known side effects for the cancer subject.

It is yet a further object of the present invention to provide novel treatment methods that may be combined with other known cancer treatments or serve as an adjunct cancer treatment so as to minimize side effects of such other cancer treatments.

It is yet another object of the present invention to provide novel cancer treatment methods that may be self-applied or self-administered by the cancer subject.

The novel cancer treatment methods of the invention include a step of applying remote conditioning to the cancer subject. Remote conditioning may include one or more episodes of exposing the cancer subject to a controlled sublethal biological stress, such as short-term ischemia of a limb. Remote conditioning may be used to upregulate or release at least one or perhaps a variety of remote conditioning substances that may provide a health benefit to the cancer subject including slowing down the proliferation of cancer cells or reducing inflammation or other harm caused by other cancer treatments.

DETAILED DESCRIPTION OF PREFERRED EMBODIMENTS OF THE INVENTION

The following description sets forth various examples along with specific details to provide a thorough understanding of claimed subject matter. It will be understood by those skilled in the art, however, that claimed subject matter may be practiced without one or more of the specific details disclosed herein. Further, in some circumstances, well-known methods, procedures, systems, and/or components have not been described in detail in order to avoid unnecessarily obscuring claimed subject matter. The illustrative embodiments described in the detailed description and claims are not meant to be limiting. Other embodiments may be utilized, and other changes may be made, without departing from the spirit or scope of the subject matter presented here. It will be readily understood that the aspects of the present disclosure, as generally described herein, can be arranged, substituted, combined, and designed in a wide variety of different configurations, all of which are explicitly contemplated and make part of this disclosure.

As mentioned above, cancer initiation and progression may involve microRNAs. MicroRNAs are 19- to 25 mer non-coding RNAs that regulate genes expression. There are over 1,000 microRNAs and only a few hundred have been closely studied to date. MicroRNAs have important biological functions in normal subjects, including regulation of cell proliferation, differentiation and apoptosis. Moreover, dysregulation of microRNAs is shown to play a critical role in carcinogenesis and cancer progression. Many microRNAs are present at lower levels in cancer tissue than in normal tissue, a state that contributes to cancer progression.

Various mechanisms are known to affect tumor growth and proliferation of malignant cells. One example of such mechanism is associated with mTOR kinase, which acts downstream of phosphoinositide 3-kinase/Akt to regulate cellular growth and metabolism. This signaling pathway is frequently dysregulated in a variety of human cancers, such as renal cell cancer, breast cancer, gastric cancer, hepatocellular carcinoma, colorectal cancer, pancreatic cancer, neuroendocrine tumors and lymphoma. In particular, up to 60% of colorectal cancers exhibit high levels of activated Akt(9), suggesting involvement of mTOR in the aberrant cell growth process. It has been reported that mTOR is highly activated in glandular elements of colorectal cancer and in colorectal adenomas with high-grade intraepithelial neoplasia, with a correlation between immunohistochemical staining intensity and depth of infiltration. mTOR generally exists in two functionally distinct complexes: mTORC1 (containing mTOR, Raptor, etc.) and mTORC2 (containing mTOR, Rictor, etc.). An increased expression of mTOR, Raptor and Rictor microRNA was also demonstrated in more advanced stages of this disease. In addition, mTOR, Raptor and Rictor protein levels have been demonstrated to be significantly elevated in stage IV colorectal cancer subjects. These clinical observations have led to the association of higher grade colorectal malignancies with increased expression of mTOR and its complexes. Disrupted mTOR pathway (leading to faster proliferation of malignant cells) may be associated with diminished levels of microRNA-144 or microRNA-451. An increase in microRNA-144/451 cluster may therefore restore Akt signaling pathways and normalize mTOR leading to reducing the spread and growth of such cells.

According to the present invention, the mechanisms of cancer development and in particular the mechanisms of proliferation and growth of malignant cells by mTOR and Akt signaling pathways may be beneficially affected (slowed down or normalized) by a natural upregulation and release of certain substances as a result of exposing the cancer subject to remote conditioning.

Another aspect of cancer treatment according to the present invention is combining the methods involving remote conditioning as described below with another known cancer treatment. Many cancer therapies are known today to be effective in inducing tumor-selective cell death, such as for example a chemotherapy. However, resistance to chemotherapeutics is a significant obstacle to the long-term treatment and survival for at least some, if not a significant portion of cancer subjects. In lung cancer for example, there exist many approved pharmaceuticals for treating non-small-cell lung cancer, such as DDP, paclitaxel, docetaxel, gemcitabine and others. The association of certain microRNAs as regulators of malignancy and apoptosis has been reported previously. According to the present invention, natural upregulation of these substances for example microRNA 144/451 cluster as a result of applying remote conditioning may be used to increase the sensitivity and vulnerability of tumor cells to chemotherapy or another cancer treatment, such as radiation therapy, drug therapy, immunotherapy, and complementary and alternative medical treatments—and therefore improve the clinical efficacy of the chemotherapy or other cancer treatments.

A further aspect of the present invention is increasing cell survival resulting from bone marrow or stem cell transplantations. Such cells may not be able to fully adapt to the new host conditions in the body of the cancer subject—therefore diminishing the efficacy of such treatment. In embodiments, application of remote conditioning may be used to increase the rate of survival of such transplanted cells and therefore improve the efficacy of this known cancer treatment.

Described herein novel cancer treatment methods may be used for a variety of cancers, including lung cancers (in particular non-small cell lung cancers), skin cancers, brain cancers, liver cancers, colorectal cancers, gastric cancers, head and neck cancers, liposarcomas, thyroid cancers, bone cancers, bladder cancers, breast cancer, and other cancers.

For the purposes of this description, the term "conditioning" is defined to mean the application of a controlled biological stress to obtain a specific health benefit or mitigate against an anticipated negative health effect. Furthermore, the term "remote conditioning" is used herein to describe a single or a plurality of repeated intermittent applications of a sub-lethal controlled biological stress to one or more suitable tissue beds or the whole body of the subject. Importantly, these repeated intermittent applications of controlled biological stress may be conducted over predefined periods of time and alternated with predefined periods of time when the biological stress is withdrawn—so as to allow for a biological recovery to take place inbetween applications of the biological stress. The notion of "remote" in the term "remote conditioning" is used to define the circumstances where the health benefit is defined in a tissue bed or an organ other than the tissue bed, which is used to apply the biological stress, which may also include the whole body.

Remote conditioning is generally known to provide a variety of health benefits to the subject. One known example is remote ischemic conditioning, in which a series of intermittent occlusions of blood flow to a suitable tissue bed (for example a leg or an arm of the subject) is known to provide protection against subsequent ischemia-reperfusion injury. For patients with a heart attack for example, such therapy has been shown to significantly reduce the size of the final myocardial infarction.

The present invention is generally concerned with using remote conditioning to provide a health benefit to the cancer subject. Such benefit may include slowing down of tumor cell proliferation or a cytoprotective effect on healthy cells when another cancer treatment (such as radiation or chemotherapy) is applied, therefore diminishing the side effects of such another cancer treatment.

In particular, remote conditioning may be used to naturally or endogenously upregulate a complex of microRNAs such as for example microRNA-1, microRNA-133 or a microRNA-144/451 cluster. That in turn may provide a health benefit for cancer subjects with diminished levels of these microRNAs by restoring their level closer to normal. An increase in the levels of these microRNAs may in turn return to normal the rate of cell proliferation and diminish the progression of cancer.

Remote Conditioning Timing Considerations

Applications of the biological stress for the purposes of applying remote conditioning to the cancer subject may be activated for predefined periods of time and may be alternated with predefined periods of time when the biological stress is withdrawn. Periodic cessation of applying the biological stress may allow the body of the cancer subject to recover and biologically adapt to the applied stress by releasing at least one or likely a plurality of beneficial remote conditioning substances into the blood stream.

In embodiments, a single application of the biological stress may be sufficient to cause a desired release of remote conditioning substances in the blood stream of the cancer subject. In other embodiments, repeated applications of the biological stress alternated with periods of biological recovery may be needed to fully activate this process. In further embodiments, the number of such intermittent applications of the biological stress may be anywhere between two and ten. In other embodiments, the number of applications of the biological stress may be three times, four times, five times, or six times—together constituting a single application of remote conditioning.

Remote conditioning procedure (consisting of one or more applications of the sublethal biological stress to the subject) may be applied once or may be applied repeatedly from time to time on a predefined schedule. In embodiments, such procedure may be applied every 1 hour, 2 hours, 6 hours, 12 hours, 24 hours, 36 hours, 48 hours, 72 hours, 96 hours, 1 week, 2 weeks, 1 month or at other even or uneven time intervals. The schedule of such applications may be determined by a physician in advance of the treatment. In embodiments, such schedule may be adjusted from time to time depending on the condition of the subject or a presence of certain confounding factors that may be acting to reduce the efficacy of remote conditioning. Examples of such confounding factors may be advanced age, diabetes, hyperlipidemia or other diseases. Adjustments to intensity and frequency of remote conditioning may also be conducted to achieve a desired level of release of remote conditioning substances by periodically monitoring their level in the target tumor or in the blood stream. Such monitoring may be conducted for example by using any available methods to detect the levels of desired microRNAs, such as 144/451 cluster.

A duration of time when the biological stress is applied during remote conditioning intervention may specified depending on the nature of the biological stress. For example, for ischemic stress, hypoxia, or changing temperature, such duration of stress may be from about 30 seconds to about 20 minutes. For radiation exposure, such duration may be as short as a small fraction of a second. The term "about" is used herein to mean plus or minus ten percent of the cited parameter. In embodiments, for an ischemic stress, the duration of its application may also be a function of a specific tissue bed to which such ischemic stress is applied. For a limb of the cancer subject, such ischemic stress may be applied for at least one minute at a time. In embodiments, each application of ischemic stress to the limb of the cancer subject may be lasting for two minutes, three minutes, four minutes, five minutes, six minutes, seven minutes, eight minutes, nine minutes, ten minutes, twenty minutes, thirty minutes or any duration of time inbetween these durations.

The duration of applying the biological stress may be the same between successive applications of the biological stress or different. In embodiments, the first duration of applying the biological stress may be longer then subsequent durations. In other embodiments, each duration of applying the biological stress may vary starting from minimal time when biological response may be initially detected and extending to the maximal time when the biological response and adaptation to the biological stress has reached its maximum.

The duration of time when the biological stress is withdrawn may generally vary from a minimal time when at least some degree of biological recovery or adaptation may be detected and extending to the maximum time when repeating the application of the biological stress is no longer effective and treated by the body of the cancer subject as a de-novo stress. This may be the case when remote conditioning substances are downregulated to be close to their native dormant levels and off their high level resulting from application of the biological stress. Such periods of cessation of the biological stress may be even or uneven between applications of the stress and may depend on the nature of the biological stress itself. For example, for ischemic stress, the periods of cessation of ischemia and restoration of blood flow may vary between about 30 seconds and 30 minutes. In other embodiments, such periods of ischemia withdrawal and restoration of blood flow may vary between about three minutes and ten minutes. For other types of the biological stress, the periods of biological recovery may take much longer. For example, for exposure to radiation or exposure to a toxic substance, the period of biological recovery may take hours, days or even weeks.

Importantly, both the periods of applying the biological stress and the periods of withdrawal of the biological stress may be selected to assure that no lasting or permanent damage is done to the selected tissue bed of the whole body of the cancer subject as a result of applying the biological stress. In that sense, the biological stress may be described as sub-lethal.

Another consideration in selecting the proper way to apply the biological stress for the purposes of remote conditioning is the degree of intensity of the stress itself. Such degree may vary from having the biological stress being minimally effective to the degree when further increase may not cause an increase in remote conditioning efficacy or the stress may no longer be considered sub-lethal. For example, the degree of ischemic stress may be varied by the size of the tissue bed subjected to the ischemia. It is generally believed that a temporary occlusion of a blood flow to a small tissue bed (a finger for example) may not be sufficient to cause a systemic remote conditioning response, while applying the ischemic stress to more than one limb may not cause an additional increase in efficacy in comparison with a single limb application thereof. The intensity of the biological stress may also be adjusted depending on the underlying conditions of the cancer subject. Certain underlying conditions may diminish the effect of the biological stress requiring its intensity to be increased to be fully effective. Examples of such underlying conditions include advanced age or diabetes.

A further timing consideration according to the present invention is when to apply remote conditioning while another cancer treatment is applied in parallel. A combined method of treating cancer may include application of remote conditioning in addition to one or more of other traditional treatments of cancer. Such known treatments may include chemotherapy, radiation therapy, cancer surgery, bone marrow or stem cell transplantation, drug therapy, immunotherapy, and complementary and alternative medical treatments.

According to the present invention, the bloodstream of the cancer subject may be enhanced by the presence of remote conditioning substances or humoral factors released as a result of remote conditioning. The process of such release may be complex. More than one beneficial remote conditioning substance may be released to reach their respective peaks at various times. Taking this complex release process into consideration when contemplating another cancer treatment may provide the most benefit to the cancer subject, for example by timing remote conditioning to maximize the presence of beneficial remote conditioning substances during another treatment or to maximize protection of healthy cells from side effects of such another treatment, such as may be the case for example with chemotherapy or radiation therapy.

Depending on the type of the biological stress used for applying remote conditioning to the cancer subject, there may be more than one optimum time window to combine remote conditioning with another treatment. For example, for remote conditioning done using limb occlusion and ischemic stress, a first period of time to do so may be during the first so-called "window of protection" and a second period of time may be during the second window of protection. In embodiments, the first window of protection may start from the time of completion of remote conditioning (or shortly before then, for example after completion of 50% or 75% of remote conditioning) and last for up to six hours afterwards. In other embodiments, such first period of time may commence upon completion of remote conditioning and last for two hours afterwards.

The second period of time for the second window of protection may start from about 24 hours following the completion of remote conditioning and last for up to 96 hours afterwards. The delay in the onset of the second window of protection may be explained by the nature thereof, which is dependent on changing gene expressions and the internal synthesis of certain beneficial proteins, a process that takes time to be effective. Other types of the biological stress may necessitate other preferred windows of time for applying another cancer treatment. In embodiments, such period of time may generally start at the completion of remote conditioning and extend for up to 6 hours afterwards.

Once the preferred timing of remote conditioning in relation to another treatment is established, both treatments may be repeated on a parallel predefined schedule such as for example one or two times per week or one or more times per month. Remote conditioning treatments may also continue further after completion of the prescribed series of another treatment.

In further embodiments, remote conditioning may be repeatedly applied on a scheduled basis so that the cancer subject has a continuously high level of circulating remote conditioning substances, for example once every one, two, or three days as may be the case with remote ischemic conditioning. In addition to providing various health benefits to the cancer subject, this method may allow for another cancer treatment to be done at any time as prescribed by a physician—irrespective of the timing considerations for remote conditioning.

Types of a Biological Stress Suitable for Remote Conditioning

In embodiments, a variety of biological stresses may be suitable for the purposes of applying remote conditioning to the cancer subject. The application of remote conditioning may be conducted using an intermittently repeated single biological stress or by applying more than one biological stress to the same cancer subject—either one at a time or by more than one biological stresses applied consecutively, in an overlapping manner or in parallel to each other.

In embodiments, application of the biological stress may be tightly controlled—at least in terms of the timing and their intensity as described above as well as in the following portions of this description illustrating various suitable biological stresses in greater detail.

Ischemic stress is a known biological stress suitable for inducing remote conditioning. Intermittent periods of substantial reduction or full cessation of blood flow to a suitable tissue bed is known to cause a protective remove conditioning effect in a subject to which it is applied. In embodiments, blood flow may be reduced to a level of 10 percent or less of the normal unobstructed blood flow to the same tissue bed. Interruption of blood flow may be conducted a number of times, such as any number of times between two and ten. The duration of each blood flow interruption may vary from about 30 seconds to about 30 min and may be either the same or different between successive episodes of ischemic stress. Restoration of blood flow inbetween the periods of blood flow occlusion allows for adaptive biological response and may last anywhere from about 1 minute to about 30 minutes.

In a typical scenario, blood flow to a limb of the cancer subject may be interrupted non-invasively by using an inflatable cuff placed about that limb and applying sufficient air pressure to the cuff so as to cause limb ischemia. Three or four cycles of 5 min limb occlusions alternated with 5 min of limb release may constitute a sufficient procedure of remote conditioning.

In addition to using a manually inflated blood pressure cuff or a manually-applied tourniquet, a variety of devices are known in the art to be configured for automated periodic cuff inflations and deflations for the purposes of applying remote ischemic conditioning to a subject. Examples of such devices are discussed in my U.S. Pat. Nos. 8,114,026; 8,753,283; and 8,795,323, these documents are incorporated herein in their respective entireties by reference.

A strong benefit of using such devices is that they are so simple to use that they can be self-applied by the cancer subject. In that sense, repeated applications of remote conditioning may be safely and effectively conducted by the cancer subject at home, therefore saving substantial healthcare expenses associated with a visit to a hospital or a clinic as is the case with other cancer treatments.

Remote ischemic conditioning may also be applied using an indwelling device with an inflatable internal balloon configured for arterial occlusion, as is also described for example in my U.S. Pat. No. 8,114,026—which may be preferred for a hospitalized cancer subject with other existing indwelling catheters and devices.

In addition to being non-invasive when applied to a limb of the subject, remote ischemic conditioning has been shown in multiple clinical trials (conducted for other indications) to be extremely safe. As compared with other known cancer treatments such as chemotherapy or radiation therapy, there are no known side effects of remote ischemic conditioning—a welcome relief for treating physicians allowing using this treatment method rather liberally without being concerned with damage to healthy surrounding tissues and cells.

In addition to releasing various remote conditioning substances that may directly benefit the cancer subject (such as microRNA 144/451 cluster), remote ischemic conditioning may be used for providing a systemic anti-inflammatory effect for the cancer subject and as such can further benefit the cancer subject when other cancer treatments are applied at the same time.

Hypoxia is another biological stress, which may be repeatedly administered to the cancer subject. Hypoxic remote conditioning may be administered by intermittently lowering the oxygen content in the air, which is breathed in by the cancer subject. Normal oxygen content in air is about 21 percent. Techniques and breathing devices are known to allow reduction of oxygen content to a therapeutically beneficial but still sub-lethal level, such as for example between 10 percent and 16 percent. Air with reduced oxygen content may be supplied to the cancer subject through a breathing mask or the cancer subject may be placed into a small confined space filled with such air. Hypoxic remote conditioning may be applied by breathing intermittently through the mask and alternating with normal breathing of ambient air. Alternatively, the cancer subject may enter the confined space to breathe low oxygen air for predetermined periods of time and alternate with breathing ambient air outside such confined space.

Periods of time for breathing low oxygen air as well as normal ambient air may vary from a few minutes such as 3-10 minutes to a few hours at a time. Three to ten cycles of hypoxic conditioning may be applied during a single remote conditioning session. Repeated sessions of hypoxic remote conditioning may be applied from time to time using a predefined schedule. In embodiments, a sleeping tent may be provided for the cancer subject to sleep in for such purpose. Such sleeping tent or enclosure may be equipped with a device to vary oxygen content based on a predetermined hypoxic conditioning protocol.

In embodiments, hypoxic conditioning may be applied using normal atmospheric pressure or reduced atmospheric pressure, such as to simulate high altitude/low oxygen conditions. To achieve this at sea level, a hypobaric chamber may be used to induce cancer subject breathing at periodically lowered atmospheric pressure combined or overlapped with intermittent drops in oxygen content according to the predefined hypoxic conditioning treatment protocol. The extent of lowering ambient pressure may be sufficient to simulate high altitude conditions from about 5,000 feet to about 15,000 feet.

Change in temperature may be used as a further biological stress for the present invention. Such change may be applied as an intermittent increase in body temperature by applying heat to the cancer subject; or as an intermittent cooling of the body temperature by applying cold to the cancer subject; or as an intermittent combination of heating alternated with cooling.

The extent of temperature elevation may be adjusted from normal body temperature of 37 degrees C. to about 43 degrees C. so as not to exceed natural "high fever" conditions. The extent of lowering body temperature may be from the same normal level down to about 32-35 degrees C., also known as mild hypothermia. In embodiments, body temperature may be reduced until the onset of shivering and then slightly raised to avoid such shivering.

The predetermined periods of time for induction and withdrawal of temperature change as a way to apply thermal remote conditioning may be from 3-5 minutes to 1-2 hours at a time. Three to ten cycles of temperature change may be applied to the cancer subject for the purposes of providing a single session of thermal remote conditioning.

While the body temperature may be regulated using indwelling catheters with built-in heat exchangers, it may be beneficial to use non-invasive equipment to cause a change in body temperature. In some embodiments, heat lamps, heating mattresses and heating blankets may be used to intermittently raise body temperature of the cancer subject. In other embodiments, skin contacting pads may be placed in close contact with the body of the cancer subject and warming or cooling fluid may be circulated therethrough to cause respective increase or decrease of skin temperature. Sufficient skin exposure to such pads may be needed to cause rapid enough warming or cooling of the cancer subject body. A combination of the torso, back, thigh, and optionally arm pads may be used to achieve such sufficient skin exposure.

In further embodiments, the body of the cancer subject may be submerged into a bath with a circulating fluid. The temperature of such fluid may be intermittently changed by a controller according to the predefined thermal remote conditioning protocol.

Electrical stimulation of suitable target nerves or tissue beds is another biological stress for the present invention. Such stimulation may be applied using internal electrodes or external skin electrodes. It may also be applied using electro-acupuncture needles or electrodes, such as for example described in the U.S. Pat. No. 6,836,686 incorporated herein by reference. For safety reasons, external skin electrodes may be preferred. In embodiments, electrical stimulation may be applied intermittently to the whole body of the cancer subject or to a target tissue bed or a group of nerves. For example, such stimulation may be applied to a single limb of the cancer subject such as a leg. A pair of skin electrodes may be used in this case such that the electrical current can travel from a first electrode to the second electrode. More than two electrodes may also be used.

Remote conditioning treatment protocol may specify duration of applying and withdrawal of the electrical stimulation, which may be selected to be from about 1 second to about 2 hours at a time. In further embodiments, the duration of applying the electrical stimulation as well as duration for recovery and biological adaptation when the electrical stimulation is withdrawn may be 1 sec; 5 sec; 20 sec; 30 sec; 45 sec; 1 min; 2 min; 3 min; 5 min; 10 min; 15 min; 20 min; 30 min; 45 min; 60 min; 90 min; 120 min or any time inbetween. Remote conditioning by electrical stimulation may be applied once or repeated on a predetermined schedule.

A suitable controller may be electrically coupled with skin electrodes and configured to manually or automatically deliver a remote conditioning treatment according to a predefined protocol. Suitable devices for applying electrical stimulation are described in the U.S. Pat. Nos. 6,023,642 and 5,183,041 incorporated herein in their respective entireties by reference. The controller for such electrical stimulation may be configured to apply between 2 and 20 cycles of such electrical stimulation. In embodiments, the controller may be programmed to automatically apply these electrical stimulation cycles consecutively 2 times; 3 times; 4 times; 5 times; 6 times; 10 times; 15 times; 20 times or any other number of times inbetween. Electrical parameters of this stimulation may include the extent of electrical current applied to the cancer subject (which may vary from about 10 mA to about 500 mA); voltage (which may vary from about 1 V to 150 V); frequency (which may vary from 0 to about 500 Hz); and duty cycle (which may vary from about 10 percent to about 90 percent). Remote conditioning of a cancer subject may further be applied using techniques and devices described in the US Patent Application Publication Nos. 2009/0220585; 2010/0292755; and 2013/0317581, all of which are incorporated herein by reference in their respective entireties.

Exposure to light may be conducted using various light wavelengths ranging from infrared, to near-infrared, to visible light, to ultraviolet spectrum. Single wavelength, multiple wavelengths or preferred ranges of wavelengths may be used for this purpose. The source of suitable light may include one or more lamps, LEDs, lasers or other known devices emanating light.

Specific tissue beds may be used for intermittent application of light. In embodiments, tissues with high concentration of mitochondria may be more suitable for this purpose as mitochondria is known to participate in protective mechanisms of remote conditioning. More specifically, muscles and brain neurons may be used for light exposure. In case of the brain, a helmet may be provided containing a plurality of LED or laser light sources and configured to fit around the head of the cancer subject. Near-infrared or red light may be used for intermittently and non-invasively applying a remote conditioning intervention to the cancer subject.

In embodiments, light exposure may be applied for a predefined period of time selected to be from about 1 minute to about 120 minutes. In further embodiments, the duration of light exposure per cycle may be the same or different between the cycles and may be 1 min; 3 min; 5 min; 10 min; 20 min; 30 min; 45 min; 60 min; 90 min, 120 min or anytime inbetween. The periods of biological recovery when the light is turned off may also range between about 1 min and about 120 min. In embodiments, the duration of light withdrawal may be the same or different between the cycles and may be 1 min; 3 min; 5 min; 10 min; 20 min; 30 min; 45 min; 60 min; 90 min, 120 min or anytime inbetween.

The intensity of light and other light characteristics may be selected to be effective in propagating stress to the target tissue but yet not cause any long-term or permanent tissue damage—and in that sense they may be considered sublethal. The number of cycles of light exposure may be between 2 and 20 cycles. In embodiments, the controller configured to turn the lights ON and OFF may be programmed to automatically activate cycles of light exposure consecutively 2 times; 3 times; 4 times; 5 times; 6 times; 10 times; 15 times; 20 times or any other number of times inbetween. In other embodiments, different clusters of lights may be activated or turned off at various times so as to apply intermittent light exposure to various tissue beds in a parallel or an overlapping manner.

Radiation exposure may be conducted on a repeated and intermittent basis to a target tissue bed or the whole body of the cancer subject as yet another biological stress. While other types of radiation may be useful such as radionuclide or photon, ionizing radiation may be preferred for the purposes of this invention and specifically the X-Ray gamma radiation may be useful as its biological effects are better documented in the literature.

Radiation therapy is of course a known cancer treatment. However, for the purposes of the present invention, radiation exposure may be conducted differently in a number of important aspects: (i) the target of radiation exposure may or may not be the tumor itself; (ii) the intensity of radiation may be selected to be sublethal, as opposed to delivering a lethal local dose to eradicate the tumor cells; (iii) the duration of exposure and intervals between subsequent exposures may be selected given the guidance provided below rather than what is done for traditional cancer radiation treatment.

As is generally suggested elsewhere in this description, the dosage of each individual cycle of remote conditioning may be selected to be at least strong enough to cause at least some biological adaptation response and yet not exceed the threshold of causing lasting or permanent tissue damage. For radiation exposure, such dosage may be selected to exceed at least about 3-5 Gy (300 to 500 rad). In embodiments, radiation doses to the cancer subject may depend on the size of the subject as well as the length of exposure, with exemplary skin dose rates ranging from about 5 mGy/min to about 100 mGy/min. In embodiments, the rate of radiation dose may be 5, 10, 15, 20, 30, 40, 50, 60, 70, 80, 90, 100 mGy/min or any level inbetween. Exposure times for each cycle may range from about 5 min to about 75 min. In embodiments, the exposure time may be 5, 10, 15, 20, 30, 40, 50, 60, 70, 75 min or any duration inbetween. The period of rest and biological adaptation inbetween radiation exposure may vary from 5 min to several days and even weeks. In embodiments, the period of withdrawal of radiation may be 5, 10, 15, 20, 30, 40, 50, 60, 90, 120, 180 min or any duration inbetween. In other embodiments, the duration of rest may be 1, 2, 3, 4, 5, 6, 7, 10, 14, 21 days or any duration inbetween. The number of radiation exposure cycles may range from 2 to 10 and may be 2, 3, 4, 5, 6, 7, 8, 9, or 10 cycles.

Toxic substance exposure on a repeated basis is yet another example of a biological stress used to induce remote conditioning according to the present invention. A variety of toxic substances in sublethal doses may be ingested, inhaled, injected or otherwise administered to the cancer subject. Toxic substances with known biological effects may be preferred for use for the method of the invention as compared with other less known toxic substances. Examples of toxic substances with known biological effects are inhalation of smoke, injection of chemical therapy agents, narcotics, etc.

As with radiation exposure, toxic substance exposure for remote conditioning purposes may be guided by different principles as compared with traditional cancer chemotherapy. In particular, the following differences are highlighted: (i) the target of toxic exposure may or may not be the tumor itself, the toxic substance may be delivered systemically or locally to a healthy tissue bed other than that containing the tumor; (ii) the degree of toxicity may be selected to be sublethal, as opposed to a lethal local dose of a chemical agent given to eradicate the tumor cells; (iii) the choice of the toxic substance, duration of treatment and intervals between subsequent toxic exposures may be selected given the need to elicit a remote conditioning response rather than what is done for traditional cancer chemotherapy.

Application of pain is yet another example of controlled biological stress. Pain may be non-invasively applied using a variety of applicators equipped with sharpened protrusions. Such applicators may be applied to selected skin areas and maintained there for desired periods of time. Such periods of time when pain applicators are applied and withdrawn may be the same as that described above for ischemic stress. In embodiments, pain may also be periodically applied by using a suitable pharmacological agent.

Blood donation or withdrawal of blood components may be considered a biological stress for the purposes of this invention. Periodic withdrawal of blood from the cancer subject may be conducted with intervals of time between such donations such as 1 day, 2 days, 3 days, 1 week, 2 weeks, 3 weeks, 4 weeks, 6 weeks, 8 weeks or any time inbetween. Withdrawn blood or components thereof may or may not be useful for transfusions to other subjects—the main purpose of withdrawing blood is to apply the biological stress of a controlled loss of a predetermined blood volume.

In embodiments, the volume of withdrawn blood may vary depending on the frequency of blood donations as well as the general condition of the cancer subject. The volume of blood donation may be 20 cc, 50 cc, 100 cc, 150 cc, 200 cc, 250 cc, 300 cc, 400 cc, 500 cc (one unit of blood), 600 cc, 700 cc, 800 cc, 900 cc, 1,000 cc, 1,200 cc, 1,500 cc or any volume inbetween. The volume of blood may be adjusted between donations to accommodate a change in condition of the cancer subject.

In embodiments, either whole blood or certain blood components may be withdrawn as a biological stress of the invention. In case when withdrawal of whole blood is not considered appropriate, the cancer patient may undergo periodic plasmapheresis or dialysis sessions during which only specified blood components (such as plasma for example) may be withdrawn while other components (such as platelets, red blood cells, or target microRNAs for example) may be returned to the cancer subject.

In further yet embodiments, the whole blood may be first withdrawn from the cancer subject, followed by temporary storage of this blood outside the body of the cancer subject, and finally followed by a partial or complete return of this blood to the body of the cancer subject. The duration of the temporary storage of blood outside the body of the cancer subject may be selected to be 1 min, 5 min, 10 min, 15 min, 20 min, 30 min, 45 min, 1 hr, 2 hrs, 4 hrs, 6 hrs, 12 hrs, 24 hrs or any time inbetween. The volume of temporarily withdrawn blood may be selected to be 20 cc, 50 cc, 100 cc, 150 cc, 200 cc, 250 cc, 300 cc, 400 cc, 500 cc (one unit of blood), 600 cc, 700 cc, 800 cc, 900 cc, 1,000 cc, 1,200 cc, 1,500 cc or any volume inbetween.

Pharmacological substance to simulate effects of remote conditioning or triggering of temporary adaptive biological responses thereto may also be administered to the cancer subject for the methods of the present invention. A single or several pharmacological substances may be administered either once or on a scheduled program to the cancer subject in a dosages sufficient to cause a remote conditioning effect.

Examples of a pharmacological substance useful for the purpose of the invention may include an anesthetic agent, such as propofol, sevoflurane, or another volatile anesthetic. Other examples of such pharmacological substances include adenosine, acadesine, bradykinin-2, opioid, $CB_2$, endocannabinoid, cyclosporine, angiotensin-1, nicorandil, prostaglandil, metoprolol, $H_2O_2$, diazoxide, erythropoietin, $Na^+$—$H^+$ exchange inhibitors, cariporide, and various other compounds that are described in the literature as mimicking the effects of remote conditioning or activating at least in part some of the mechanisms involved therein. Further examples of such pharmacological substances may be found in an article by I. Andreadou et al. entitled "Alternative Pharmacological Interventions that Limit Myocardial Infarction", published in 2008 in Current Medical Chemistry; as well as an article by Maurits T. Dirksen et al entitled "Reperfusion injury in humans: A review of clinical trials on reperfusion injury inhibitory strategies", published in Cardiovasc Res (2007) 74 (3): 343-355; and further in an article by DJ Hausenloy entitled "Myocardial ischemia-reperfusion injury: a neglected therapeutic target" as published in the Journal of Clinical Investigation in 2013; 123(1):92-100, all of these articles are incorporated herein by reference in their respective entireties.

In other embodiments, several spaced apart injections of muscle-stimulating drugs may be used as a biological stress for the methods of the invention. For example, spaced apart injections of epinephrine may be used to stimulate the heart several times to trigger release of remote conditioning substances.

In addition to mimicking the biological stress itself, pharmacological substances may be selected to cause the same or similar biological adaptive reaction to such stress without applying the biological stress itself. Such adaptive reaction may be reducing the levels of released reactive oxygen species, upregulating the release of RISK or SAFE kinases, preventing the opening of the mitochondrial permeability transition pores, normalizing levels of certain microRNAs (such as microRNA-1, microRNA-133a, microRNA-133b, microRNA-144/451 cluster, microRNA-338-3p), activating signal transducer and activator of transcription 3 (STAT3), reducing inflammation, etc.

The herein described subject matter sometimes illustrates different components or elements contained within, or connected with, different other components or elements. It is to be understood that such depicted architectures are merely examples, and that in fact many other architectures may be implemented which achieve the same functionality. In a conceptual sense, any arrangement of components to achieve the same functionality is effectively "associated" such that the desired functionality is achieved. Hence, any two components herein combined to achieve a particular functionality may be seen as "associated with" each other such that the desired functionality is achieved, irrespective of architectures or intermedial components. Although the invention herein has been described with respect to particular embodiments, it is understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

What is claimed is:

1. A method of increasing survival rate of bone marrow or stem cells transplanted to a cancer subject comprising the following steps:
   applying a cancer treatment to a cancer subject, said cancer treatment having a risk of depleting native bone marrow or stem cells in said cancer subject;
   transplanting bone marrow or stem cells to said cancer subject, and
   applying remote ischemic conditioning to said cancer subject, wherein said remote ischemic conditioning includes a plurality of repeated intermittent applications of an ischemic stress to a limb of said cancer subject cancer subject, said intermittent applications are conducted non-invasively by intermittently reducing or occluding blood flow to a limb of said cancer subject according to a predefined remote ischemic conditioning schedule over predefined periods of time alternated with predefined periods of time when application of said ischemic stress is withdrawn.

2. The method as in claim 1, wherein said step of applying remote conditioning further comprising providing an automatic device for performing intermittent occlusions of blood flow to said limb.

3. The method as in claim 2, wherein said automatic device is configured for activation by said cancer subject, whereby said method is adapted for self-administration by said cancer subject.

4. The method as in claim 1, wherein said step of applying remote ischemic conditioning includes adjusting of intensity or frequency of said remote ischemic conditioning to be sufficient for reaching a target level of release of a remote conditioning substance beneficial for said cancer subject.

* * * * *